United States Patent [19]
Gatt et al.

[11] Patent Number: 5,492,924
[45] Date of Patent: Feb. 20, 1996

[54] PHORBINE DERIVATIVES AND THEIR USE IN THE DIAGNOSIS AND THERAPY OF CANCER

[75] Inventors: Shimon Gatt; Arie Dagan, both of Jerusalem, Israel; René Santus, Crépy en Valois; Jean-Claude Maziére, Brunoy, both of France; J. Donald Chapman, Elkins Park; Edward L. Engelhardt, Huntingdon Valley, both of Pa.

[73] Assignees: Fox Chase Cancer Center, Philadelphia, Pa.; The French National Institute of Health and Medical Research (Inserm), Paris, France; Yissum Research Development Company of the Hebrew University of Jerusalem, Jerusalem, Israel

[21] Appl. No.: 126,361

[22] Filed: Sep. 24, 1993

[51] Int. Cl.$^6$ .................. A61K 31/40; C07D 487/22
[52] U.S. Cl. .............................. 514/410; 540/145
[58] Field of Search .................. 540/145; 514/410

[56] References Cited

U.S. PATENT DOCUMENTS

| | | | |
|---|---|---|---|
| 4,604,241 | 8/1986 | Sakata et al. | 540/145 |
| 4,675,338 | 6/1987 | Bommer et al. | 514/410 |
| 4,709,022 | 11/1987 | Sakata et al. | 540/145 |
| 4,849,207 | 7/1989 | Sakata et al. | 424/1.1 |
| 4,965,064 | 10/1990 | Karasawa et al. | 540/145 |
| 4,971,991 | 11/1990 | Umemura et al. | 514/410 |
| 4,977,177 | 12/1990 | Boomer et al. | 540/145 |
| 4,996,312 | 2/1991 | Sakata et al. | 540/145 |
| 5,002,962 | 3/1991 | Pandey et al. | 514/410 |
| 5,004,811 | 4/1991 | Boomer et al. | 540/145 |
| 5,093,349 | 3/1992 | Pandey et al. | 514/410 |
| 5,169,944 | 12/1992 | Nelson et al. | 540/145 |
| 5,198,460 | 3/1993 | Pandey et al. | 514/410 |

FOREIGN PATENT DOCUMENTS

| | | |
|---|---|---|
| 248282A1 | 8/1987 | Germany . |
| 58-981 | 1/1983 | Japan . |
| 60-81128 | 5/1985 | Japan . |
| 61-83185 | 4/1986 | Japan . |
| 63-4805 | 2/1988 | Japan . |
| 63-101384 | 5/1988 | Japan . |
| 63-196586 | 8/1988 | Japan . |
| 63-239286 | 10/1988 | Japan . |
| 63-243025 | 10/1988 | Japan . |
| 63-290881 | 11/1988 | Japan . |
| 64-61481 | 3/1989 | Japan . |
| 2-49664 | 10/1990 | Japan . |
| 3284681 | 12/1991 | Japan . |
| 4139186 | 5/1992 | Japan . |

OTHER PUBLICATIONS

Pandey et al., Bioorganic & Medicinal Chem. Letters vol. 2, No. 5 pp. 491–496, 1992.
Joerg G. Moser, Pros. SPIE–Int. Soc. Opt. Eng., 1881:116–125 (1993).
Masaya Ishihara et al., Photomedicine and Photobiology, 12:121–126 (1990).
H. Kawabe et al., Photodynamic Therapy and Biomedical Lasers (P. Spinelli et al., eds.), 820–825 (1992).
Ravindra K. Pandey et al., Bioorganic & Medicinal Chemistry Letters, 2:491–496 (1992).
Ravindra K. Pandey et al., Pros. SPIE–Int. Soc. Opt., 1645:264–273 (1992).
S. Nakajima et al., Journal of Photochemistry and Photobiology, B: Biology, 7:189–198 (1990).

*Primary Examiner*—Mukund J. Shah
*Assistant Examiner*—Pavanaram K. Sripada
*Attorney, Agent, or Firm*—Dann, Dorfman, Herrell and Skillman

[57] ABSTRACT

Phorbine derivatives having high potency and light absorptivity in the 650 to 780 nanometer range are useful in cancer diagnosis and therapy, especially photodynamic therapy.

13 Claims, 1 Drawing Sheet

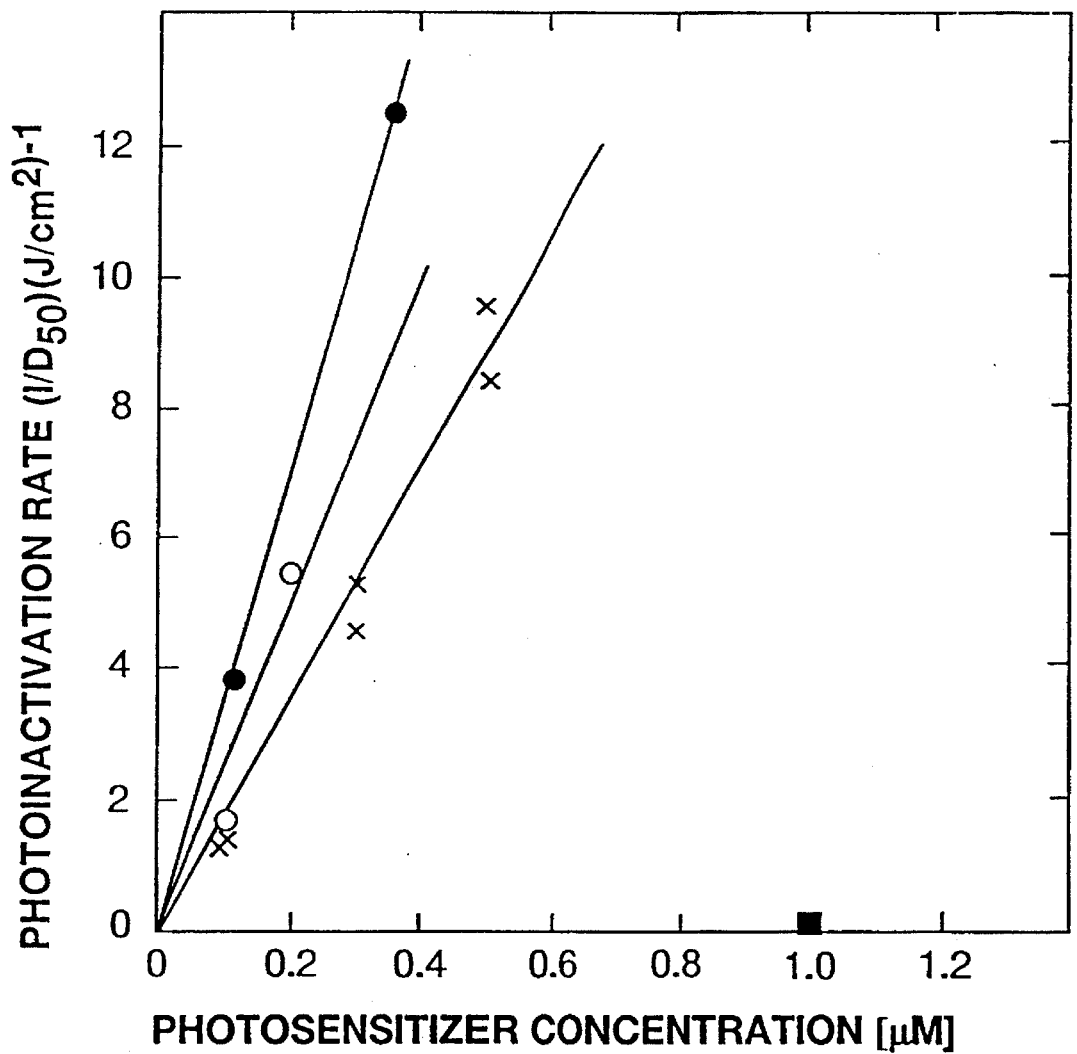

PHORBINE DERIVATIVES AND THEIR USE IN THE DIAGNOSIS AND THERAPY OF CANCER

Pursuant to 35 U.S.C. §202(c), it is hereby acknowledged that the U.S. Government has certain rights in the invention described herein, which was made in part with funds from the National Institutes of Health (Grant No. R01 CA52102).

FIELD OF THE INVENTION

The present invention relates to phorbine derivatives, compositions containing such derivatives and their use in cancer diagnosis and therapy. More particularly, this invention relates to certain pheophorbide and bacteriopheophorbide compounds, formulations of such compounds and their application in photodynamic therapy (PDT).

BACKGROUND OF THE INVENTION

PDT is an experimental cancer treatment modality under investigation as an alternative treatment for the local control of drug- and radiation-resistant tumors. It requires the combination in tumor target cells of a photosensitive compound, activating light and molecular oxygen. Excited singlet-state photosensitizer undergoes transition to a triplet-state which can react with molecular oxygen to produce singlet oxygen, the putative cytotoxin for PDT. Singlet oxygen is a highly reactive form of oxygen which can react with several biomolecules.

In clinical practice, a patient undergoing PDT receives an intravenous injection of the photosensitizing compound and twenty-four to seventy-two hours later the tumor is exposed to light of appropriate wavelength, e.g., from a dye laser directed through optical fibers to illuminate tissue through diffusing fibers or lens. Dosimetry and method of light delivery are dependent upon the size of the tumor and its location.

Monoamides of an aminocarboxylic acid and a tetrapyrrole, including pheophorbide a, bacteriopheophorbide a and pyropheophorbide a, have been disclosed for use in PDT and photodiagnosis of tumors. See, for example, U.S. Pat. No. 4,977,177 to J. Bommer and B. Burnham.

Most of the early PDT studies have been performed with hematoporphyrin and hematoporphyrin derivatives. Photofrin®, one of the photosensitizing compounds currently in clinical use for PDT, consists of a mixture of monomer, polymer and aggregate forms of various porphyrins. It has taken several years of research to determine the cellular uptake, the pharmacokinetics and the biological effectiveness of the different molecular components within this photsensitizing preparation.

The clinical experience to date with porphyrin derivatives has not been entirely satisfactory. It has been found that porphyrin derivatives are metabolized and cleared from the patient's system relatively slowly. Consequently, the clinical use of such photosensitizers has been marked by rather severe cutaneous phototoxicity, requiring patients to remain protected from sunlight for periods of up to 4–6 weeks. Furthermore, the tissue penetrating effect of the porphyrin derivatives previously tested has been suboptimal, rendering the use of such compounds impractical for the treatment of relatively large tumors.

Because of their retention by, and destructive effect on cancer cells, the use of photosensitizing compounds in PDT continues to be an area of active investigation. However, a need exists for new photosensitizing agents in the form of single compounds of well defined structure, which produce singlet oxygen at high yield when activated by light of wavelength greater than 630 nm and which exhibit reduced normal tissue phototoxicity and superior tissue penetration, so as to overcome the above-noted drawbacks in the use of photosensitizing compounds reported to date.

SUMMARY OF THE INVENTION

In accordance with one aspect of the present invention, phorbine derivatives are provided having the formula:

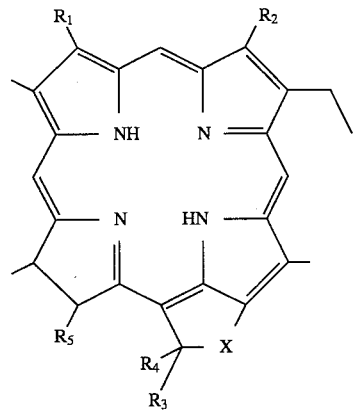

wherein X represents C=O or C—OH;

$R_1$ represents —CH=$CH_2$ or —$COCH_3$;

$R_2$ represents lower alkyl of $C_1$–$C_6$ carbon atoms, —$CH_2$—OH, or CHO (formyl);

$R_3$ and $R_4$ may be the same or different and represent —H, —OH, —COOH or $CO_2$— lower alkyl of $C_1$–$C_6$; and $R_5$ represents —$(CH_2)_2$—CO—NH—$(CH_2)_m$—$(Y)_n$—$(CH_2)_p$—Z, wherein Y represents —O—,

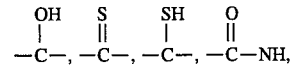

and —S—, Z is selected from the group consisting of OH, O-lower alkyl of $C_1$–$C_6$, $CH_3$, SH, S-lower alkyl of $C_1$–$C_6$, $SO_3^-$, or $PO_3^-$ and m is an integer from 1 to 12; n is 1 or 0 and p is an integer from 1 to 6, or 0, provided that when n is 1 p≠0.

According to another aspect, the present invention provides compositions comprising Compounds of the foregoing formula with a biologically compatible vehicle for use in cancer diagnosis or therapy, especially PDT.

According to a further aspect, the present invention provides methods of using photosensitizer compounds of the foregoing formula in the practice of PDT or photodiagnosis, the latter utility employing the compounds as such, or in the form of complexes with radioactive metals.

The photosensitizer compounds of the invention are especially useful in PDT as they exhibit superior potency compared to prior art compounds, sufficient tissue penetration to enable treatment of relatively large tumor volumes, and relatively rapid cell clearance, so as to minimize phototoxicity in normal cells.

BRIEF DESCRIPTION OF THE DRAWING

The sole FIGURE of the drawing is a graphical representation of data showing the photoinactivation rate for representative phorbine derivates of the invention, in comparison to a clinically tested standard, in the treatment of tumor cells in vitro, as a function of concentration.

DESCRIPTION OF PREFERRED EMBODIMENTS

The term "phorbine derivative" is used herein to refer to compounds having the following nucleus, in which the ring positions are numbered in accordance with convention.

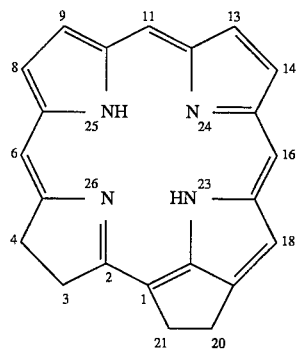

It is contemplated, in accordance with this invention, that the two nitrogen-bound hydrogen atoms in the above formula may be replaced with a metal atom or ion to yield a metallo-phorbine complex having diagnostic and/or therapeutic activity which may be approximately the same as, or appreciably different from that of the uncomplexed compounds.

The phorbine derivatives of the invention are of the general formula:

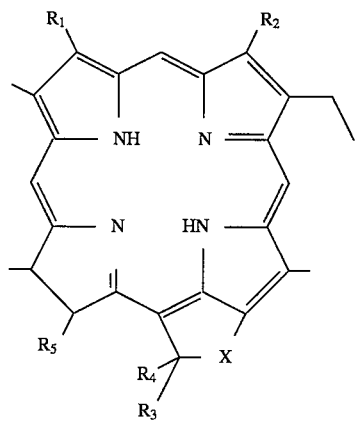

wherein X represents C=O or C—OH;

$R_1$ represents —CH=CH$_2$ or —COCH$_3$;

$R_2$ represents -lower alkyl of $C_1$–$C_6$ carbon atoms, —CH$_2$—OH, or —CHO (formyl);

$R_3$ and $R_4$ may be the same or different and represent —H, —OH, —COOH or —CO$_2$— lower alkyl of $C_1$–$C_6$; and $R_5$ represents —(CH$_2$)$_2$—CO—NH—(CH$_2$)$_m$—(Y)$_n$—(CH$_2$)$_p$—Z, wherein Y represents —O—,

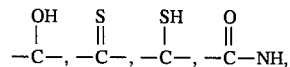

and —S—, Z is selected from the group consisting of OH, O-lower alkyl of $C_1$–$C_6$, CH$_3$, SH, S-lower alkyl of $C_1$–$C_6$, SO$_3^-$, or PO$_3^-$ and m is an integer from 1 to 12; n is 1 or 0 and p is an integer from 1 to 6, or 0, provided that when n is 1 p≠0.

A preferred embodiment of the invention includes compounds of formula I, above, in which $R_5$ represents —(CH$_2$)$_2$—CO—NH—(CH$_2$)$_{m_1}$—Z$_1$ wherein Z$_1$ is selected from the group consisting of OH, O-lower alkyl of $C_1$–$C_6$ or CH$_3$ and $m_1$ is an integer from 1–8, particularly preferred compounds being those of formula I known as pheophorbides (X=C=O; $R_1$=—CH=CH$_2$; $R_2$=—CH$_3$; $R_3$=—CO$_2$CH$_3$; $R_4$=H), bacteriopheophorbides (X=C=O; $R_1$=—COCH$_3$; $R_2$=—CH$_3$; $R_3$=—CO$_2$CH$_3$; $R_4$=H) and pyropheophorbides (X=C=O; $R_1$=—CH=CH$_2$; $R_2$=—CH$_3$; $R_3$ and $R_4$=H.

Most preferred are 9-ethenyl-14-ethyl-21-(methoxycarbonyl)-4,8,13,18-tetramethyl-20-oxo-N-(4-hydroxybutyl)-3-phorbinepropanamide having the formula:

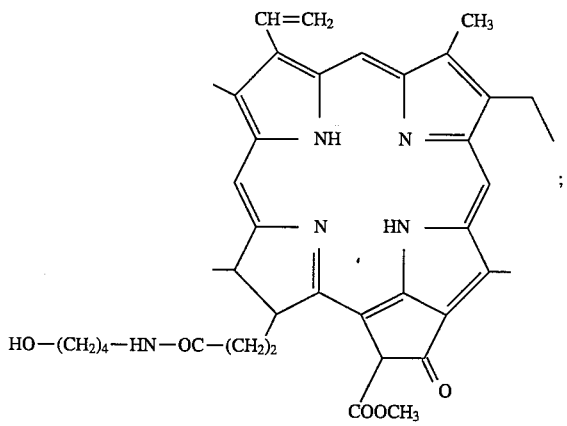

9-ethenyl-14-ethyl-21-(methoxycarbonyl)-4,8,13,18-tetramethyl-20-oxo-N-(6-hydroxyhexyl)-3-phorbinepropanamide having the formula:

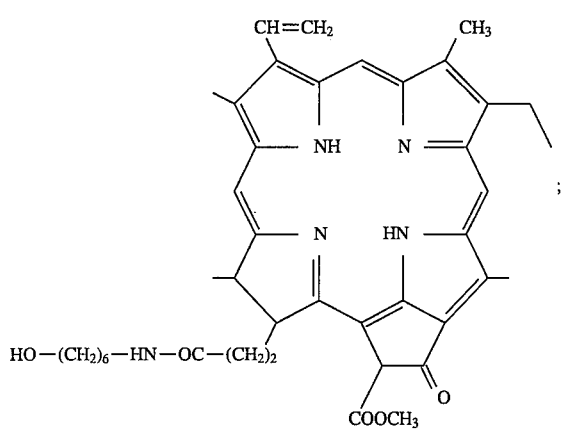

and 9-acetyl-14-ethyl-13,14-dihydro-21-(methoxycarbonyl)-4,8,13,18-tetramethyl-20-oxo-N-(4-hydroxybutyl)-3-phorbinepropanamide having the formula:

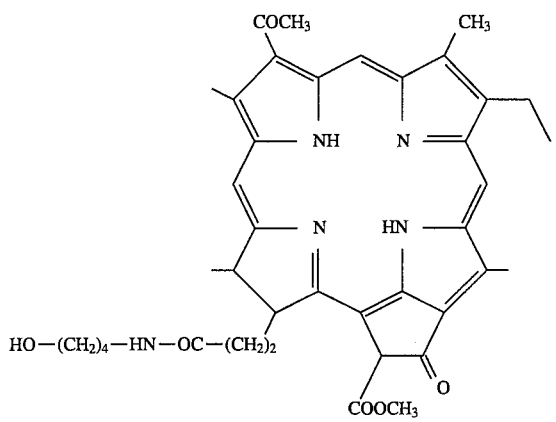

The selected pheophorbide starting material (substituted 3-phorbinepropanoic acid) is converted to the substituted amide by production of an active ester intermediate through reaction with N-hydroxysuccinimide or 1-hydroxybenzotrizole and dicyclohexylcarbodiimide. The active ester then is condensed with the selected amine compound to give the desired substituted 3-phorbinepropanamide.

The pheophorbide a starting material can be conveniently prepared from *Spirulina platensis*. The bacteriopheophorbide a can be prepared from membranes derived from cultures of *Rhodobacter capsulatus*.

Purification of the desired product can be carried out in the manner exemplified hereinbelow.

The phorbine derivatives of the invention may be used for diagnosis and therapy with respect to a broad range of tumors, including endobronchial lung cancer, oesophageal cancer, superficial bladder cancer, ovarian cancer, cerebral tumor and prostatic cancer, to name a few. For purposes of diagnosis, the tumor to which the photosensitizer compound is introduced must be capable of selectively fluorescing when exposed to light of appropriate wavelength. For purposes of therapy, the tumor must be penetrable by the energy source used for activation of the photosensitizer compound. The appropriate wavelength of light for diagnostic purposes may be from 360–760 nm, whereas light activating energy for PDT is generally in the range of 600–800 nm, the preferred compounds absorbing in the 650–780 nm range. Light of such longer wavelength better enables penetration into the tumor volume for therapeutic purposes. As those skilled in the art will recognize, the exact light dosimetry is ultimately dependent on the size and location of the tumor.

Although the source of light energy for diagnosis and/or therapy is limited, laser light is preferable because it can be delivered at a pre-determined wavelength and selectively applied.

In diagnostic applications, the photosensitizer compound of the invention is administered to the patient, and thereafter light of appropriate wavelength is applied to the area to be examined. Internal organs can be examined in this manner using light provided by an endoscope. The fluorescence emitted by the illuminated tumor renders the tumor visible by appropriate light detectors.

In PDT applications, an appropriate dose of the photosensitizer compound is administered, and, after a prescribed interval, the tumor is irradiated using laser light of appropriate wavelength delivered by any of various light-emitting elements which are familiar to those skilled in the art.

In practicing PDT using the phorbine derivatives of the invention, the normal interval between administration of the photosensitizer and irradiation by laser light, to allow sufficient time for distribution of the photosensitizer in the tumor, is usually between 1 and 48 hours.

Laser light of appropriate wavelength and intensity for practicing PDT in accordance with this invention can be provided by a dye laser pumped by an argon ion or copper vapor laser (600–710 nm) or a titanium saphire laser pumped by an argon ion or copper vapor laser (700–900 nm). Such laser systems are capable of delivering light at wavelengths between 600 and 900 nm with a total power output of at least 800 mw and up to 4 W. Laser systems satisfying these parameters are available from various commercial sources.

As compared to Photofrin®, the phorbine derivatives of the invention have a far greater photoinactivation rate as a function of concentration, and thus appear to be substantially more potent than Photofrin®. The greater potency of the photosensitizer compounds of the invention should allow utilization of relatively lower doses, thereby attenuating normal tissue phototoxicity in patients receiving PDT.

The dose of the phorbine derivatives of the invention that is administered to a patient will vary depending on whether the purpose is diagnostic or therapeutic. In the case of diagnosis, doses on the order of 0.5 mg/kg will be effective and up to about 5 mg/kg may be used. In the case of PDT, the appropriate dose will generally be in the range of about 0.3–3 mg/kg. In view of the relatively higher potency of the photosensitizer compounds of the invention, doses at the lower end of the aforesaid range should be effective.

Pharmaceutical preparations comprising the phorbine derivatives of the invention may be conveniently formulated for administration with a biologically acceptable vehicle. According to a preferred embodiment, the pharmaceutical preparations of the invention include the patient's own serum or serum fractions. Other suitable vehicles may include mixtures of physiological saline with detergents, e.g., TRITON X-100®, TWEEN-80® with solvents, such as dimethylsulfoxide (DMSO), or within liposomes. The concentration of the phorbine derivative in the chosen vehicle should normally be from about 0.25 mg/ml to about 5 mg/ml. In all cases, any substance used in formulating a pharmaceutical preparation of the invention should be virus-free, pharmaceutically pure and substantially non-toxic in the amount used.

If necessary, the action of contaminating microorganisms may be prevented by various antibacterial and antifungal agents, such as parabens, chlorobutanol, phenol, surbic acid, thimerosal and the like. It will often be preferable to include in the formulation isotonic agents, for example, glucose or sodium chloride.

As used herein, the term "biologically acceptable vehicle" is intended to include any and all solvents, dispersion media and the like which may be appropriate for the desired route of administration of the pharmaceutical preparation. The use of such vehicles for photosensitizer compounds of the type described herein is known in the art. Except insofar as any conventional vehicle is incompatible with the photosensitizer compounds described herein, its use in the pharmaceutical preparations of the invention is contemplated.

It is especially advantageous to formulate the pharmaceutical preparation in dosage unit form for ease of administration and uniformity of dosage. "Dosage unit form" as used herein refers to a physically discrete unit of the pharmaceutical preparation appropriate for the patient undergoing diagnostic examination or treatment. Each dosage should contain the quantity of phorbine derivative calculated to produce the desired diagnostic or therapeutic effect in association with the selected vehicle. Procedures for determining the appropriate dosage unit for photodiagnosis or phototherapy in a particular tumor type are well known to those skilled in the art. The preferred dosage form is provided as an injectable solution (isotonic).

The pharmaceutical preparation of the invention is preferably administered parenterally, intravenous administration being the most preferred route. Other modes of administration may also be effective, such as oral, intraperitoneal, intratumoral, intramuscular or subcutaneous administration. The proper fluidity for the selected mode of administration of the formulation can be maintained, e.g., by the use of surfactants.

The following examples are provided to describe the invention in further detail. These examples, which set forth the best mode presently contemplated for carrying out the invention, are intended to illustrate and not to limit the invention.

Examples 1–6 describe the synthesis and purification of representative photosensitizer compounds of the present invention.

EXAMPLE 1

9-Ethenyl-14-ethyl-21-(methoxycarbonyl)-4,8,13,18-tetramethyl-20-oxo-N-(4-hydroxybutyl)-3-phorbinepropanamide (Ph4-OH)

Pheophorbide a, 250 µmol, was dissolved in 25 mL of dichloromethane in a round bottom flask, protected from moisture by a stream of nitrogen and cooled in an ice-bath. N-hydroxysuccinimide, 260 µmol, was added to the solution, followed by 350 µmol of dicyclohexylcarbodiimide. The mixture was stirred 4 hours by a magnetic stirrer. The solvent then was removed on a rotary evaporator and the oily residue dissolved in 30 mL of acetonitrile. 4-Aminobutanol, 500 µmol, dissolved in 30 mL of 2-propanol:water, 1:1 then was added dropwise to the stirred solution over a period of 30 minutes at room temperature. The mixture was stirred for an additional 4 hours then transferred to a separatory funnel and partitioned between 150 mL of dichloromethane and 50 mL of water. After washing with two 50 mL portions of water, the organic layer was dried over magnesium sulfate, filtered and evaporated to dryness. The residue was dissolved in 10 mL of dichloromethane and applied to a 2×30 cm column of silica gel [E. Merck silica gel 60 (70–230 mesh)] prepared under dichloromethane. The column was eluted with 300 mL of dichloromethane, then 200 mL of acetonitrile followed by 400 mL of dichloromethane:methanol (8:2). The product was found in the dichloromethane:methanol eluate. The fractions containing the product were identified by thin layer chromatography using E. Merck silica gel 60 on aluminum foil plates, developed in chloroform:methanol:0.01N sulfuric acid (80:20:2). The yield was 200 µmol (80%).

EXAMPLE 2

9-Ethenyl-14-ethyl-21-(methoxycarbonyl)-4,8,13,18-tetramethyl-20-oxo-N-(6-hydroxyhexyl)-3-phorbinepropanamide (Ph6-OH)

The method of Example 1, above, was followed except that 500 µmol of 6-aminohexanol was substituted for the 4-aminobutanol. The yield of the desired product was 190 µmol (75%).

EXAMPLE 3

9-Ethenyl-14-ethyl-4,8,13,18-tetramethyl-20-oxo-N-(6-hydroxyhexyl)-3-phorbine propanamide (PyPh6-OH)

Pyropheophorbide a, 200 µmol was converted to the activated ester with N-hydroxysuccinimide and dicyclohexylcarbodimide as described for pheophorbide a in Example 1, above. This intermediate, dissolved in 50 mL of acetonitrile, was added dropwise to a stirred solution of 300 µmol of 6-aminohexanol in 50 mL of 2-propanol, contained in a 250 mL flask provided with a magnetic stirrer. The mixture was stirred for 4 hours, then transferred to a 500 mL separatory funnel with 100 mL of dichloromethane. The solution was extracted with 4×50 mL of water. The organic phase was dried over magnesium sulfate and the solvent evaporated. The residue was dissolved in 10 mL of dichloromethane and applied to a 2×40 cm silica gel column [E. Merck silica gel 60 (70–230 mesh)] prepared in dichloromethane. The column was eluted with 200 mL of dichloromethane, followed by 200 mL dichloromethane:methanol (9:1), 200 mL dichloromethane:methanol (4:1) and 400 mL dichloromethane (7:3). Fractions containing the product, as evidenced by TLC, were combined. The TLC plates were E. Merck silica gel 60 on aluminum foil. The developing solvent was dichloromethane:methanol: 0.02 N sulfuric acid 85:15:15. The yield was 200 µmol (66%).

EXAMPLE 4

9-Acetyl-14-ethyl-13,14-dihydro-21-(methoxycarbonyl)-4,8,13,18-tetramethyl-20-oxo-N-(4-hydroxybutyl)-3-phorbinepropanamide (BPh4-OH)

Bacteriopheophorbide a, 100 µmol was dissolved in 5 mL of chloroform contained in a 25 mL round bottom flask, cooled in an ice-bath and protected from moisture by an Argon atmosphere. 1-Hydroxybenzotriazole hydrate, 100 µmol was added and the mixture stirred 15 minutes. Dicyclohexyl carbodiimide, 300 µmol then was added and stirring continued for 2 hours. The chloroform was evaporated and the residue dissolved in 5 mL of 2-propanol. To the magnetically stirred solution was added a solution of 0.5 mmol of 4-aminobutanol in 5 mL of 2-propanol. The mixture was stirred for 5 hours, then transferred to a separatory funnel with 40 mL of dichloromethane. The mixture was extracted with 2×40 mL of water and the organic phase dried over magnesium sulfate. The solvent was evaporated on a rotary evaporator, the residue taken up in 5 mL of dichloromethane and applied to a 2×20 cm column of silica gel [E. Merck silica gel 60 (70–230 mesh)]. The column was eluted with 200 mL of dichloromethane, then with 200 mL of acetonitrile followed by 300 mL of dichloromethane: methanol (1:1). Fractions containing the product were identified by TLC on E. Merck silica gel on aluminum foil plates. The yield was 55 µmol (55%).

EXAMPLE 5

Purification of Ph6-OH

The instrument employed was a Waters Delta Prep 3000, using a 10×300 mm DELTA PAK 15µ$C_{18}$-100 Å column. The solvent system was 75% acetonitrile, 25% triethylamine phosphate buffer at pH 3.2 The flow rate was 20 mL/minute. Detection was by light absorbance at 410 nm. A 10 mg sample, dissolved in 5.0 mL of acetonitrile was injected.

The major product peak (area 47.4%) had a retention time of 36.97 minutes. This fraction (volume, 72 mL) was partitioned between 450 mL of dichloromethane and 400 mL of water. The dichlorometahne layer was separated, washed with five additional 400 mL portions of water, dried over sodium sulfate and evaporated to give 1.25 mg of product.

Analytical HPLC showed this product to be 99.4% pure.

Mass spectrometry showed a molecular ion at m/z, 692 daltons (M+), $C_{41}H_{49}N_5O_5$ requires 692.

EXAMPLE 6

Purification of Ph4-OH

The same instrument and column employed in Example 5 were again used. The solvent was methanol-water (88 parts MeOH to 12 parts $H_2O$, by volume). Flow rate was 20 mL/minute. Detection was by light absorbance at 410 nm. A 10.2 mg sample, dissolved in 10 mL of the same methanol-water mixture and filtered, was injected.

The major product peak (area 80.8%) had a retention time of 30.8 minutes. The main product fraction (about 125 mL) was concentrated on a film evaporator (bath temperature below 40° C.). When most of the methanol had been removed, a green solid separated. The solid was dissolved in dichloromethane and the dichloromethane layer separated and evaporated in a stream of dry nitrogen. After drying over phosphorus pentoxide in vacuo, the product weighed 3.7 mg (recovery, 44.9%).

Analytical HPLC showed this product to be 97.3% pure.

Mass spectrometry showed a molecular ion at m/z 664 daltons ($M^+$). $C_{39}H_{45}O_5$ requires 664.

The phorbine derivatives prepared as described above may be treated with a metal compound, e.g., a metal halide, in a suitable solvent, with heating, to yield metallo-phorbine complexes in which the metal replaces the two nitrogen-bound hydrogens in the phorbine nucleus. Representative metals for the formation of such complexes include Si, Mn, Fe, Co, Ni, Zn, Ga, In, Sn, Sm, Eu, Gd, Tc and Tl. Certain isotopes of these metals, such as $^{67}$Ga, $^{111}$In, $^{201}$Tl, $^{99m}$Tc are radioactive. The radiation emitted by complexes comprising such metals may be utilized in cancer diagnosis and/or therapy.

Examples 7–11 set forth the results of biological testing of representative photosensitizer compounds of the invention in the treatment of tumors.

EXAMPLE 7

Administration of Photosensitizer In Vivo

Photosensitizers of the "phorphyrin class" may be extremely hydrophobic and require special procedures of solubilization for in vivo administration. Photofrin® is supplied as a lyophilized powder which is dissolved (suspended) in 5% dextrose solution for i.v. administration to both animals and humans. Other preclinical studies have solubilized novel photosensitizers in saline/DMSO mixtures, saline/detergent mixtures (e.g., 10% TWEEN-80®) and liposome suspensions. Pheophorbide and bacteriopheophorbide photosensitizers in accordance with this invention were solubilized in 100% DMSO and were diluted with 9 additional parts of pure serum fraction from respective host prior to in vivo injection. DMSO concentration in the final solution (suspension) was 10–15%. Both the mouse and rat tumor hosts showed no adverse reactions when fetal calf serum was used in place of mouse or rat serum. Other studies with these pheophorbide photosensitizers have shown that they can complex with serum albumin, low density lipoprotein (LDL) and high density lipoprotein (HDL). The role of these lipid-transporting molecules of the blood for delivery of pheophorbide and bacteriopheophorbide photosensitizers to target cells in animal tumors has not been fully elucidated.

EXAMPLE 8

Delivery of Activating Light to Tumor Treatment Volumes

As previously noted, tumor response after PDT results from damage to vascular and/or tumor cells by $^1O_2$ produced by photochemical reaction. Cell response, including cell killing, results from oxidative damage to cellular molecules, especially to cellular membranes. The efficient production of this highly reactive form of oxygen within target cells requires the appropriate combination of photosensitizing agent and light intensity at the wavelength which matches the photosensitizer absorption spectra. Light of 630 nm wavelength is used to activate a relatively weak absorbance of Photofrin®. Both the pheophorbide and bacteriopheophorbide photosensitizers of the invention display relatively strong absorption spectra near to 670 and 750 nm, respectively. Photodosimetry studies with living tumor tissue have indicated that light of 670 nm wavelength can penetrate tumor tissue 25–30% more efficiently than can 630 nm light. This physical gain of light penetrance could have clinical significance for the treatment of superficial lesions of various body organs. Photodosimetry studies have also shown a two-fold increase of light penetration in tumor tissue at wavelengths of 730 nm and greater. Such a gain in light penetrance indicates that solid tumor volumes can be illuminated with relatively uniform light intensity by interstitial illumination techniques analogous to those currently used for isotope brachytherapy. The spacing of implanted needles in which laterally-diffusing optical fibers can be placed for tumor illumination can be 1.0 cm and greater at these higher wavelengths. Consequently, bacteriopheophorbide photosensitizers activated by 750 nm light are the preferred drug for the PDT treatment of solid tumors and interstitial illumination the preferred mode of light delivery.

EXAMPLE 9

Photosensitizing Effectiveness
of Ph4-OH on Tumors in Vivo

Photosensitizer efficacy was measured with two different tumor models. Solid EMT-6 tumors (~0.1 cm$^3$) growing on the backs of C.B17/Icr scid mice were exposed to 300J of 670 nm light one hour after the iv administration of Ph4-OH. Light was generated by a laser, transported to the tumor-bearing mouse via an optical fiber and focused onto the tumor surface through a diffusing lens. The light dose rate at the tumor surface was 200–400 mW/cm$^2$ and the field size encompassed the tumor cross section. Photodosimetry studies indicated that intra-tumor light dose would decrease to ~0.5 at the tumor base relative to the tumor surface. EMT-6 tumor response was quantified by two different assays. At various times after PDT treatment, animals were sacrificed, tumors were removed in toto from the animal and mechanically disrupted. Tumor cells were released by an enzyme digestion procedure. Released tumor cells were plated into Petri dishes for colony forming assays. When this procedure was performed immediately after PDT treatment, there was little or no killing observed, as is evident from the data in Table A, even for treatments which led to complete cures of tumors if left in their hosts. It can be seen from Table A that when tumors were excised 24 hr after PDT treatment, tumor cell plating efficiency decreased dramatically in proportion to photosensitizer concentration and light dose.

These data indicate that tumor response to PDT with the photosensitizer compound of the invention results from tumor perfusion shutdown and secondary ischemic tumor cell death. A comparison of photosensitizer and light doses required to produce the same extent of tumor cell kill with Ph4-OH relative to Photofrin® showed this compound to be at least fifty times more potent for producing tumor response in vivo.

Tumor response to PDT was also quantified by tumor regrowth assay. The volumes of both untreated and PDT-treated tumors in animals were estimated from caliper measurements made three times a week. Tumor response in vivo was characterized by acute inflammatory reaction observed on days 1 and 2 after treatment followed by tumor volume shrinkage and eventual cure or regrowth. These responses from individual tumors were quantified in days after treatment required for tumors to reach two times their treatment volume. Table B shows growth delays observed with various concentrations of pH 4-OH and pH 6-OH treated with 300J of 670 nm light. Tumor response is a function of photosensitizer dosage. Ph 4-OH shows the superior tumor response. In this assay, some tumor cures are consistently observed when growth delay times are 15 days and greater. Again comparisons relative to Photofrin® with respect to the photosensitizer dosage and light dose for achieving equal tumor growth delay show Ph 4-OH to be at least fifty times more potent.

Tumor response and cure was also investigated with 4-5 cm$^3$ Dunning prostate carcinomas (R3327-AT) growing in Fischer X Copenhagen rats. These tumors were illuminated by laser light delivered by a laterally-diffusing optical fiber applicator which contained seven fibers in an hexagonal array of equilateral triangles with 0.9 cm spacing. Complete tumor necrosis and response was induced by 400J of 670 nm light delivered one hour after the iv administration of 2 mg/kg Ph4-OH. This response indicated that Ph4-OH was at least eighty times more potent than Photofrin® for inducing tumor necrosis and cure in this tumor model.

TABLE A

IN VITRO PLATING EFFICIENCIES OF EMT-6
TUMOR CELLS FROM TUMORS TREATED IN VIVO
BY PDT WITH 300J OF 670 NM LIGHT
PLATING EFFICIENCY

| GROUP | IMMEDIATE EXCISION | EXCISION AT 24 HR |
|---|---|---|
| CONTROL | 0.51 ± 0.4 | — |
| 1 mg/kg Ph4—OH | 0.55 ± 0.07 | 0.001 ± 0.001 |
| 2 mg/kg Ph4—OH | 0.48 ± 0.09 | ≦0.0001 |

TABLE B

TIME FOR EMT-6 TUMORS TO GROW TO TWO
TIMES THE TREATMENT VOLUME AFTER 300J
OF 670 NM DELIVERED ONE HR AFTER I.V.
PHOTOSENSITIZER ADMINISTRATION

| PHOTO-SENSITIZER | INJECTED DOSE mg/kg | REGROWTH TIME days |
|---|---|---|
| Controls | — | 3.1 ± 0.3 |
| Ph6—OH | 0.60 | 4.7 ± 0.7 |
|  | 1.00 | 7.9 ± 1.3 |
|  | 3.00 | 25.5 ± 2.9 |
| Ph4—OH | 0.45 | 4.3 ± 0.4 |
|  | 0.75 | 8.6 ± 0.5 |
|  | 1.00 | 12.4 ± 0.6 |
|  | 1.50 | >22.0 |

EXAMPLE 10

Photosensitizing Effectiveness of Pheophorbide and Bacteriopheophorbide Derivatives with Tumor Cells In Vitro EMT-6 mouse tumor cells were exposed in slowly-stirred suspension cultures to various concentrations of Ph6-OH, Ph4-OH and BPh4-OH for one hour prior to illumination with graded light doses of specific wavelength. The pheophorbide and bacteriopheophorbide compounds were illuminated with 670 and 750 nm light, respectively. Illuminated cell populations were plated into Petri dishes containing appropriate media for colony forming assays. The surviving fraction (SF) of cells after various PDT treatments was computed from the ratio, [plating efficiency (treated cells)]/[plating efficiency (control cells)]. For each photosensitizer dosage investigated, survival curves of log SF versus light dose were constructed and analyzed. The light dose required to kill 50%, 90% and 99% of tumor cell populations ($D_{50}$, $D_{10}$ and $D_{01}$) were determined. The reciprocal of light dose required to kill 50% of a tumor cell population ($1/D_{50}$) was used as a photoinactivation rate for each concentration and as a basis for comparison of photosensitizer efficacy. Inactivation rates for the various photosensitizing agents activated with 630 (Photofrin®), 670 (Ph6-OH) and 750 (BPh4-OH) nm light are shown in the accompanying Figure. Rates of photoinactivation and relative effectiveness of the pheophorbide and bacteriopheophorbide compounds compared to Photofrin®are given in Table C. The inactivation rate for Photofrin® was extrapolated from data generated at much higher drug concentrations utilizing the same experimental protocol. The relative effectiveness of Ph4-OH and BPh4-OH are approximately 800X and approximately 1150X, respectively.

For each concentration of photosensitizer compound studied, there was a threshold dose of light below which little or no cell killing occurred. This threshold light dose was found to decrease inversely as the photosensitizer concentration was increased. For example, for PH6-OH at 0.1, 0.3 and 0.5 µM, the threshold light dose was 0.75, 0.18 and 0.08J/cm², respectively. The products of [drug concentration]×[threshold dose] for any one photosensitizing agent fall within a narrow range of constant values, indicating that the "reciprocity rule" of photosensitization was operative, at least for the low, clinically relevant photosensitizer concentrations investigated in this manner.

TABLE C

PHOTOINACTIVATION RATES AND RELATIVE EFFECTIVENESS MEASURES FOR CLAIMED PHOTOSENSITIZERS AND PHOTOFRIN ®

| Photosensitizer | Photoinactivation Rate $(J/cm^2)^{-1}$ | Relative Effectiveness |
|---|---|---|
| .3 µM Photofrin ® (■)* | 0.009 | 1 |
| .3 µM Ph6—OH (X) | 5.10 | 567 |
| .3 µM Ph4—OH (○) | 7.30 | 811 |
| .3 µM BPh4—OH (●) | 10.4 | 1156 |

*Symbols refer to photosensitizing compounds as shown in the Figure.

EXAMPLE 11

Photosensitizer Drug Uptake into Mouse Tumor and Endothelial Cells

EMT-6 mouse tumor and UNA mouse endothelial cells were exposed to various concentrations of the photosensitizer compounds of the invention in slowly-stirred suspension cultures. At various times, cell samples were separated from the drug by centrifugation and washed with media which did not contain photosensitizer. Cells were lysed and solubilized by mixing 1 mL of cell suspension with 1 mL 4% Triton X-100. After 2 hours of extraction, samples were mixed with 2 mL 95% EtOH and photosensitizer levels quantified by spectrofluorometry using $E_{ex}$=400 nm and $E_{em}$=670 nm. Photosensitizer uptake into both cell lines at 37° C. was rapid and near linear with time over the first 2–3 hours, but the rate of drug uptake slowed significantly at longer exposure times (6–12 hours). Table D shows initial rates of photosensitizer uptake into EMT-6 tumor and UNA endothelial cells exposed to 0.5 and 1.0 µM Ph 4-OH. For both cell lines, uptake is dependent upon photosensitizer concentration in the media and the larger volume tumor cells show the higher rates of uptake. If drug uptake rate is normalized to a standard cell volume, EMT-6 tumor cells bind the photosensitizer at 1.25 times that of UNA endothelial cells. These studies suggest that these photosensitizers are not preferentially taken up by endothelial cells relative to tumor cells.

TABLE D

| Concentration of Photosensitizer | Cells | Initial Binding Rate µg/10⁶ cells/hr |
|---|---|---|
| 0.5 µM | EMT-6 | 0.097 |
| 1.0 µM | EMT-6 | 0.068 |
| 0.5 µM | UNA Endothelial | 0.067 |
| 1.0 µM | UNA Endothelial | 0.038 |

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A phorbine derivative of the formula

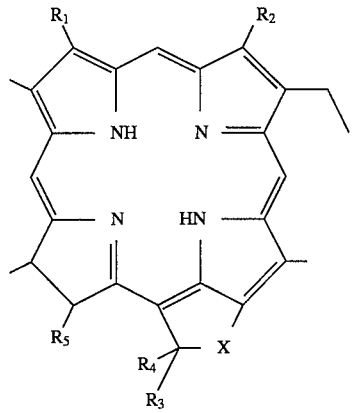

wherein X represents C═O or C—OH;

$R_1$ represents —CH═CH₂ or —COCH₃;

$R_2$ represents -lower alkyl of $C_1$-$C_6$ carbon atoms, —CH₂—OH, or CHO (formyl);

$R_3$ and $R_4$ may be the same or different and represent —H, —OH, —COOH or CO₂— lower alkyl of $C_1$-$C_6$; and $R_5$ represents —(CH₂)₂—CO—NH—(CH₂)$_m$—Z, Z being selected from the group consisting of OH, O-lower alkyl of $C_1$-$C_6$, CH₃, SH, S-lower alkyl of $C_1$-$C_6$, $SO_3^-$, or $PO_3^-$ and m is an integer from 1 to 12.

2. A phorbine derivative as claimed in claim 1, wherein $R_5$ represents —(CH₂)₂—CO—NH—(CH₂)$_{m1}$—$Z_1$, wherein $Z_1$, is selected from the group consisting of OH, O-lower alkyl of $C_1$-$C_6$ or CH₃ and $m_1$ is an integer from 1–8.

3. A phorbine derivative as claimed in claim 1, having the formula:

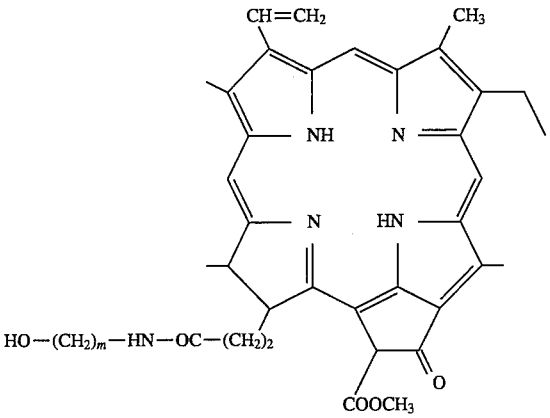

wherein m=1 to 12.

4. A phorbine derivative as claimed in claim 1, having the formula:

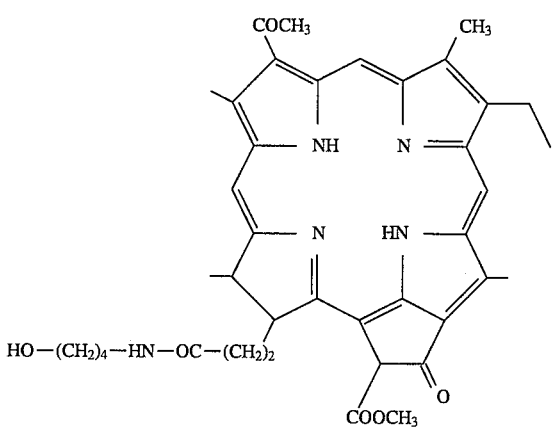

5. A phorbine derivative as claimed in claim 1, having the formula:

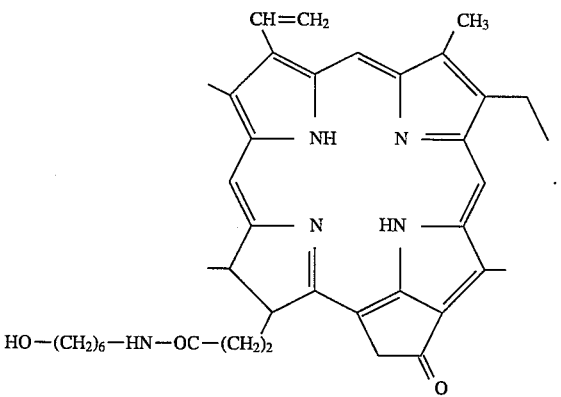

6. A composition of matter for cancer diagnosis or therapy in a patient bearing a solid tumor comprising cancer cells, said composition comprising a phorbine derivative as claimed in claim 1 and serum from said patient.

7. A composition of matter as claimed in claim 1, wherein said phorbine derivative is selected from the group of 9-ethenyl-14-ethyl-21 -(methoxycarbonyl)-4,8,13,18-tetramethyl-20-oxo-N-(4 -hydroxybutyl)-3-phorbinepropanamide; 9-ethenyl-14 -ethyl-21-(methoxycarbonyl)-4,8,13,18-tetramethyl-20 -oxo-N-(6-hydroxyhexyl)-3-phorbinepropanamide; 9 -ethenyl-14-ethyl-4,8,13,18-tetramethyl-20-oxo-N-(6 -hydroxyhexyl)-3-phorbine propanamide; and 9-acetyl-14 -ethyl-13,14-dihydro-21-(methoxycarbonyl)-4,8,13,18 -tetramethyl-20-oxo-N-(4-hydroxybutyl)-3-phorbinepropanamide.

8. A method for treating a tumor comprising cancer cells, said method comprising delivering to said tumor a therapeutically effective amount of a phorbine derivative as claimed in claim 1 and thereafter applying to said tumor light of appropriate intensity and wavelength to activate said phorbine derivative, thereby producing a killing effect on said cancer cells.

9. A method as claimed in claim 8, wherein a phorbine derivative selected from the group consisting of 9-ethenyl-14-ethyl-21-(methoxycarbonyl)-4,8,13,18 -tetramethyl-20-oxo-N-(4-hydroxybutyl)-3-phorbinepropanamide; 9-ethenyl-14-ethyl-21 -(methoxycarbonyl)-4,8,13,18-tetramethyl-20-oxo-N-(6 -hydroxyhexyl)-3-phorbinepropanamide; 9-ethenyl-14 -ethyl-4,8,13,18-tetramethyl-20-oxo-N-(6-hydroxyhexyl)-3-phorbine propanamide; and 9-acetyl-14-ethyl-13,14 -dihydro-21-(methoxycarbonyl)-4,8,13,18-tetramethyl-20 -oxo-N-(4-hydroxybutyl)-3-phorbinepropanamide is delivered to said tumor.

10. A method for detecting a solid tumor comprising cancer cells in a patient, said method comprising administering to said patient a phorbine derivative as claimed in claim 1 in an amount effective to be taken up by said tumor, applying light of appropriate wavelength to cause fluorescence of said derivative and detecting fluorescence emitted from said derivative.

11. A method as claimed in claim 10, wherein a phorbine derivative selected from the group consisting of 9-ethenyl-14-ethyl-21-(methoxycarbonyl)-4,8,13,18-tetramethyl-20-oxo-N-(4-hydroxybutyl)-3 -phorbinepropanamide; 9-ethenyl-14-ethyl-21 -(methoxycarbonyl)-4,8,13,18-tetramethyl-20-oxo-N-(6 -hydroxyhexyl)-3-phorbinepropanamide; 9-ethenyl-14 -ethyl-4,8,13,18-tetramethyl-20-oxo-N-(6-hydroxyhexyl)-3-phorbine propanamide; and 9-acetyl-14-ethyl-13,14 -dihydro-21-(methoxycarbonyl)-4,8,13,18-tetramethyl-20 -oxo-N-(4-hydroxybutyl)-3-phorbinepropanamide is administered to said patient.

12. A method for detecting a solid tumor comprising cancer cells in a patient, said method comprising administering to said patient a phorbine derivative as claimed in claim 1 complexed with a radioactive metal in an amount effective to be taken up by said tumor, and detecting radiation emitted from said radioactive metal.

13. A method as claimed in claim 12, wherein a phorbine derivative selected from the group consisting of 9-ethenyl-14-ethyl-21-(methoxycarbonyl)-4,8,13,18-tetramethyl-20-oxo-N-(4-hydroxybutyl)-3-phorbinepropanamide; 9-ethenyl-14-ethyl-21 -(methoxycarbonyl)-4,8,13,18-tetramethyl-20-oxo-N-(6 -hydroxyhexyl)-3-phorbinepropanamide; 9-ethenyl-14 -ethyl-4,8,13,18-tetramethyl-20-oxo-N-(6-hydroxyhexyl)-3-phorbine propanamide; and 9-acetyl-14-ethyl-13,14 -dihydro-21-(methoxycarbonyl)-4,8,13,18-tetramethyl-20 -oxo-N-(4-hydroxybutyl)-3-phorbinepropanamide is administered to said patient.

* * * * *